United States Patent [19]

Moseman

[11] Patent Number: 4,589,994

[45] Date of Patent: May 20, 1986

[54] LIQUID FOOT TREATMENT COMPOSITION

[76] Inventor: Roger E. Moseman, 19400 Redwing Blvd., Hastings, Minn. 55033

[21] Appl. No.: 682,656

[22] Filed: Dec. 17, 1984

[51] Int. Cl.$^4$ ............................ C11D 3/48; C11D 9/50
[52] U.S. Cl. .................................... 252/107; 252/106; 252/DIG. 14; 252/DIG. 5; 424/196.1; 514/731; 514/783
[58] Field of Search ....... 252/106, 107, 547, DIG. 14; 514/783, 731

[56] References Cited

U.S. PATENT DOCUMENTS

| | | | |
|---|---|---|---|
| 2,153,143 | 4/1939 | Figg, Jr. et al. | 87/5 |
| 2,251,934 | 8/1941 | Hartung | 252/107 |
| 2,698,301 | 12/1954 | Shumard | 252/102 |
| 2,906,664 | 9/1959 | Maurice | 252/107 |
| 3,063,895 | 11/1962 | Pearson et al. | 167/31 |
| 3,326,808 | 6/1967 | Noseworthy | 252/106 |
| 3,538,217 | 11/1970 | Dewar et al. | 424/173 |
| 3,703,472 | 11/1972 | Shaw et al. | 252/107 |
| 3,793,233 | 2/1974 | Rose et al. | 252/547 |
| 3,824,190 | 7/1974 | Winicov et al. | 252/106 |
| 3,943,234 | 3/1976 | Roggenkamp | 424/343 |
| 4,124,520 | 11/1978 | Schwalley et al. | 252/106 |
| 4,153,570 | 5/1979 | Hennemann et al. | 252/121 |
| 4,157,977 | 6/1979 | Dewar et al. | 252/106 |
| 4,371,461 | 2/1983 | Jones et al. | 252/547 |
| 4,435,317 | 3/1984 | Gerritsen et al. | 252/547 |

FOREIGN PATENT DOCUMENTS

| | | |
|---|---|---|
| 1153267 | 9/1983 | Canada . |
| 1040543 | 9/1966 | United Kingdom . |
| 1104692 | 2/1968 | United Kingdom . |
| 1311886 | 3/1973 | United Kingdom . |
| 1464716 | 2/1977 | United Kingdom . |

*Primary Examiner*—Prince E. Willis
*Attorney, Agent, or Firm*—Merchant, Gould, Smith, Edell, Welter & Schmidt

[57] ABSTRACT

Aqueous concentrates and soaking solutions effective to clean and deodorize feet, and to protect them from fungal infections are disclosed. The compositions comprise a phenolic antifungal compound and a terpenic fragrance which are dissolved or dispersed in water by means of a four-component anionic surfactant system and at least one foam-producing nonionic surfactant.

16 Claims, No Drawings

LIQUID FOOT TREATMENT COMPOSITION

BACKGROUND OF THE INVENTION

A number of compositions designed to control foot odor, perspiration and the athlete's foot fungus are commercially available. Powdered foot treatment compositions commonly employ an absorptive material such as talc or silica, in combination with active ingredients such as fragrance, deodorants and anti-fungal agents. These compositions are designed to be sprinkled onto the feet or used to impregnate socks or shoe insoles. The active ingredients can also be delivered in organic solvents via aerosol spray systems. Although such formulations may deliver effective amounts of active ingredients to sweaty or irritated feet, they suffer from a number of disadvantages. In the first place, the drying action of the absorbent particles and aerosol sprays can roughen or harden the skin of the feet, while the use of organic carrier solvents can lead to irritation. In the second place, the solid compositions are not intended to clean the feet, but rather deposit of powder which can soil shoes and clothing. Finally, compositions designed for aerosol delivery pose the risk of user inhalation of volatile solvents such as methylene chloride.

Therefore, a need exists for a foot treatment composition which will both clean the feet while delivering effective amounts of fragrance and a fungistatic agent thereto. A further need exists for a composition having a high deodorant and fungistatic activity which does not soil or unduly dry the skin of the feet.

BRIEF DESCRIPTION OF THE INVENTION

The present invention provides a liquid foot treatment composition in the form of an aqueous concentrate which can be diluted with water to form a foot-soaking bath. The aqueous concentrate comprises a four-component anionic surfactant system, at least one foamable nonionic surfactant, a fragrant terpene-rich oil and an effective amount of a phenolic anti-fungal agent. When diluted and employed periodically as a foot-soaking bath, the present composition is effective to clean the feet and eliminate fungi and odor-causing bacteria without unduly depleting the natural skin oils.

The common chemical names of the components are in accord with the CTFA Cosmetic Ingredient Dictionary (1982 ed.), and the percentages are by weight unless otherwise noted.

DETAILED DESCRIPTION OF THE INVENTION

The foot treatment compositions of the present invention are preferably formulated as liquid concentrates having an effective amount of a phenolic antifungal compound and a fragrance comprising a terpene-rich oil dispersed or dissolved in a major proportion of water with the aid of an anionic-nonionic surfactant system.

ANTIFUNGAL AGENT

The present concentrates will incorporate an amount of a phenolic compound effective to substantially reduce or eliminate the athlete's foot fungus and odor-causing bacteria. Useful phenolic biocides include phenol, m-cresol, o-cresol, p-cresol, o-phenyl-phenol, 4-chloro-m-cresol, chloroxylenol, 6-n-amyl-m-cresol, resorcinol, resorcinol monoacetate, p-tert-butyl-phenol and o-benzyl-p-chlorophenol. The biologically-active, water soluble salts of these compounds may also be employed, e.g., the alkali metal salts. Of these compounds o-benzyl-p-chlorophenol is preferred due to its high biocidal power.

TERPENE OIL

A fragrant, terpene-rich oil will be included in the present concentrates for cosmetic purposes. Preferred oils for use in the present concentrates include anise, cinnamon, clove, coriander, eucalyptus, fennel, lavender, lemon, orange, orange flower peppermint, pine, spearmint and compound bouquets thereof. Pine oils are preferred for use in the present formulations. Such oils are commonly prepared by solvent extraction or destructive distillation of pine, cedar or similar resinous woods, and can incorporate copaene, alpha-cedrene and longifolene as the major terpenic components.

SURFACTANT SYSTEM

The phenolic biocide, terpene oil and other water-insoluble adjuvants will preferably be dispersed or solubilized in the aqueous base by means of a nonionic-anionic surfactant system, which also functions to enhance the cleaning power of the composition. The predominent surfactants for use in the present concentrates are those of the anionic class. About 15–35%, preferably about 20–30% by weight of total anionic surfactants will be incorporated into the concentrates preferably as a mixture of four chemical types: (1) the salts of fatty alcohol(ethylenoxy)sulfates, (2) the salts of fatty acids, (3) the salts of fatty alcohol sulfates and the salts of alkylated aromatic sulfonates. Useful salts (M) of these surfactants include alkali metal and alkaline earth metal salts such as lithium, sodium, magnesium, potassium and ammonium.

The salts of fatty alcohol(ethylenoxy)sulfates can be represented by the general formula:

wherein n is about 6–20, preferably about 8–13; m is about 1–12, preferably 1–5 and M is as defined hereinabove, preferably ½(Mg), NH$_4$ or Na. Commercially available anionics of this type include magnesium laureth sulfate, ammonium laureth sulfate, ammonium laureth-5-sulfate, sodium deceth sulfate and sodium myreth sulfate. A preferred mixture of this surfactant class comprises magnesium laureth sulfate and ammonium laureth sulfate combined in weight ratio of about 2–3:1, respectively.

Useful common fatty acid salts include the water-soluble sodium and potassium salts of $C_{10}$–$C_{18}$-saturated and unsaturated fatty acids and mixtures thereof (the "soaps"). Commercially-available fatty acid salts useful as the soap component of the present compositions include sodium cocoate, sodium laurate, sodium palmitate, sodium tallowate, sodium stearate, sodium oleate, sodium linoleate, sodium linolenate and the like.

The anionic surfactants will also include a fatty alcohol sulfate salt wherein the fatty alcohol comprises a $C_8$–$C_{22}$-n-alkyl group, preferably a $C_{10}$–$C_{18}$-n-alkyl group. Commercially-available surfactants of this class include magnesium lauryl sulfate, ammonium $C_{12}$–$C_{15}$-alcohols sulfate, sodium $C_{16}$–$C_{20}$-alcohols sulfate, sodium cetyl sulfate, sodium steryl sulfate, sodium decyl sulfate, sodium myristyl sulfate and the like.

An alkyl-substituted(aryl)sulfonate salt, preferably of the general formula: (R)ArSO$_3$M, will also be included in the present compositions, wherein R is a $C_1$-$C_{16}$ branched or straight-chain alkyl group, and M is as hereinabove defined. R may also represent two methyl substituents. Useful surfactants of this class include ammonium xylene sulfonate, ammonium toluene sulfonate, ammonium cumene sulfonate, sodium decyl benzene sulfonate, lithium or potassium pentapropyl benzene sulfonate, sodium dodecyl benzene sulfonate, ammonium dodecyl benzene sulfonate, sodium tridecyl benzene sulfonate, sodium tridecyl benzene sulfonate and the like.

Preferably the present compositions will comprise a weight ratio of sulfonate:alkyl sulfate:soap:fatty alcohol(ethylenoxy)sulfate of about 1:2-5:10-20:25-35 respectively.

The present foot treatment composition will also include an amount of one, and preferably two nonionic surfactants, which can function to foam the present concentrates when they are diluted with warm water and which can aid in homogeneously dispersing the other constituents.

Preferred foamable nonionic detergents include the amine oxides, such as the $C_{10}$-$C_{20}$-alkyl-di(lower)alkyl-amine oxides or the [$C_{10}$-$C_{20}$-alkylamido($C_2$-$C_5$)alkyl]-di(lower)alkylamine oxides. Especially preferred members of this class include lauryl(dimethyl)amine oxide, coco(dimethyl)amine oxide (Ninox® C, Stephan Chem. Co., Northfield, Ill.), myristyl(dimethyl)amine oxide, stearyl(dimethyl)amine oxide (Schercamox® DMS, Scher Chemicals, Inc., Clifton, N.J.), coco(bis-hydroxyethyl)amine oxide (Schercamox® CMS), tallow(bis-hydroxyethyl)amine oxide and cocamidopropyl(dimethyl)amine oxide(Schercamox® C-AA).

Another useful class of nonionic surfactants are the hydroxypolyalkylenoxy(alkyl)benzene surfactants of the general formula: $C_6$-$C_{18}$-n-alkyl-phenyloxy(EtO)$_n$H wherein n is about 3-20, preferably about 5-15. Other useful surfactants of this class are disclosed in Canadian Pat. No. 729,071, the disclosure of which is incorporated by reference herein. These nonoxynol surfactants are commercially-available as the Igepal® series from GAF Corp., e.g., Igepal® CO-630 ($C_9$-alkyl, n=9) and Igepal CO-660 ($C_9$-alkyl, n=10).

The present foot treating concentrates will comprise a major proportion of water, preferably about 50-75%, most preferably about 55-65%, in combination with minor amounts of a non-toxic lower alkanol cosolvent, which can aid in the solubilization or dispersal of the phenolics, the oils, etc. Useful cosolvents will include about 1-10%, preferably about 2-5% of ethanol, isopropanol or mixtures thereof.

The present compositions can also include minor but effective amounts of adjuvants including organic hardness ion sequestering agents such as tetrasodium EDTA, acidulent agents such as ammonium chloride, preservatives such as $C_1$-$C_4$ alkyl parabens, fragrance, dye and the like. When present, these adjuvants will individually be present at about 0.01-2% of the concentrate, preferably at about 0.1-1% of the concentrate.

Therefore, preferred cleaning, deodorizing and antifungal foot treatment concentrates will include about 50-75% water, about 1-10%, most preferably about 2-5% of a lower alkanol co-solvent; about 5-25%, most preferably about 10-20% of a $C_{10}$-$C_{15}$-alkyl(ethylenoxy)sulfate salt; about 2.5-12%, most preferably about 5-10% of a fatty acid salt; about 0.5-7%, most preferably about 1-5% of a $C_8$-$C_{22}$-alkyl sulfate salt; about 0.1-5%, most preferably about 0.25-2.5% of an alkyl- or dialkyl-phenylsulfonate salt; about 0.5-7.5%, most preferably about 1-5% of a $C_{10}$-$C_{20}$-alkyl-di(lower)alkyl amine oxide; about 0.1-10%, most preferably about 0.5-5% of a terpene-rich oil, e.g., pine oil and about 0.1-10%, most preferably about 0.5-5% of a phenolic antifungal agent, e.g., o-benzyl-para-chlorophenol, and optionally, about 1-5% of (nonyl)phenyl(OEt)$_n$OH wherein n is about 5-15.

In use the concentrates will typically be diluted with warm water to a concentrate of about 0.3-1% and the resultant solution employed periodically to bathe or soak sweaty and/or dirty feet for an appropriate length of time, e.g. for 2-15 minutes. Feet thus treated are cleaned and remain deodorized and rendered resistant to infection by the athletes foot fungus for a period of at least one week.

The concentrates can be prepared by dissolving the water-conditioning agent, if any, in about 60-70% of the total water, followed by addition of the cosolvents, the surfactants, the terpenic oil and the phenolic agent, with appropriate agitation. The balance of the water is provided by the water present in the commercially-available surfactant formulations.

The invention will now be further described by reference to the following detailed example.

EXAMPLE

FOOT TREATMENT CONCENTRATE

The constituents of Table I are blended in the weight percentages and in the order listed, to yield a homogeneous liquid foot treatment concentrate.

TABLE I

| Constituent | Wt. % |
|---|---|
| Water+ | 41.6 |
| Tetrasodium EDTA (38% Active) | 1.2 |
| Ethanol | 2.5 |
| Isopropanol | 0.75 |
| Magnesium Laureth Sulfate (60% Active) | 16.70 |
| Ammonium Laureth Sulfate (60% Active) | 7.50 |
| Magnesium Lauryl Sulfate (30% Active) | 8.30 |
| Lauryl Dimethyl Amine Oxide (30% Active) | 6.70 |
| Ammonium Xylene Sulfonate (40% Active) | 1.25 |
| Soap | 8.25 |
| Pine Oil | 2.50 |
| o-Benzyl-p-chlorophenol | 2.25 |
| Ammonium Chloride | 0.50 |
| | 100.00% |

+2.5% of the water is optionally replaced by nonoxynol-9 or nonoxynol-10.

When diluted to 0.5 wt.-% with warm tap water and employed periodically as a foot-soak bath, the concentrate is effective to clean and deodorize the user's feet and protect them from fungal infection, without unduly drying or irritating the skin.

The invention has been described by reference to various specific and preferred embodiments and techniques. However, it should be understood that many variations and modifications may be made while remaining within the spirit and scope of the invention.

What is claimed is:

1. An aqueous concentrate effective to clean and deodorize feet consisting essentially of:
   (a) water;
   (b) about 15-35% of a mixture of anionic surfactants comprising
      (i) an alkylated aromatic sulfonate;
      (ii) a fatty alcohol sulfate;
      (iii) a fatty acid salt; and (iv) a fatty alcohol(ethylenoxy)sulfate wherein the salts (i)–(iv) are present in a weight ratio of about 1:2–5:10–20:25–35 respectively;
(c) about 0.5–7.5% of a $C_{10}$–$C_{20}$-alkyl-di(lower)alkylamine oxide;
(d) about 0.1–10% of an anti-fungal phenolic compound; and
(e) about 0.1–10% of a terpene-rich oil.

2. The aqueous concentrate of claim 1 wherein the fatty alcohol(ethylenoxy)sulfate salt comprises about 5–25% of a compound of the formula:

$$CH_3(CH_2)_nCH_2(OCH_2CH_2)_mOSO_3M$$

wherein n is about 6–20, m is about 1–12 and M is ½(Mg), $NH_4$ or Na.

3. The aqueous concentrate of claim 1 wherein the alkylated aromatic sulfonate salt comprises about 0.1–5% $C_1$–$C_{16}$-alkylphenyl-sulfonate or a dimethylphenylsulfonate.

4. The aqueous concentrate of claim 1 wherein the fatty acid salt comprises about 2.5–12% of a soap.

5. The aqueous concentrate of claim 1 wherein the fatty alcohol sulfate salt comprises about 0.5–7% of a $C_8$–$C_{22}$-alkyl sulfate salt.

6. The aqueous concentrate of claim 1 which further includes about 1–10% of a lower alkanol.

7. The concentrate of claim 1 wherein the terpene-rich oil comprises pine oil.

8. The concentrate of claim 1 wherein the phenolic compound comprises ortho-benzyl-para-chlorophenol.

9. The aqueous concentrate of claim 1 which further includes about 1–5% of nonylphenyl$(OEt)_n$OH wherein n is about 5–15.

10. An aqueous concentrative effective to clean and deodorize feet consisting essentially of:
(a) about 55–65% water;
(b) about 2–5% of ethanol, isopropanol or mixtures thereof;
(c) about 10–20% of fatty alcohol(ethylenoxy)sulfate salts of the formula:

$$CH_3(CH_2)_nCH_2(OCH_2CH_2)_mOSO_3M$$

wherein n is about 8–13, m is about 1–5 and M is ½(Mg), $NH_4$ or Na;
(d) about 5–10% soap;
(e) about 1–5% of a $C_8$–$C_{22}$-alkyl sulfate salt;
(f) about 0.25–2.5% of a xylene sulfonate salt;
(g) about 1–5% of a $C_{10}$–$C_{20}$-alkyl-di(lower)alkyl amine oxide;
(h) about 0.5–5% pine oil; and
(i) about 0.5–5% of a phenolic anti-fungal agent.

11. The aqueous concentrate of claim 10 wherein the phenolic agent comprises ortho-benzyl-para-chlorophenol.

12. The aqueous concentrate of claim 10 wherein the fatty alcohol(ethylenoxy)sulfate salts consist of an about 2–3:1 mixture of magnesium laureth sulfate and ammonium laureth sulfate, respectively.

13. A foot soaking or bathing solution formed by diluting the concentrate of claim 1 to about 0.3–1% with water.

14. A foot soaking or bathing solution formed by diluting the concentrate of claim 10 to about 0.3–1% with water.

15. A method of cleaning and deodorizing feet comprising periodically contacting them with the solution of claim 13.

16. A method of cleaning and deodorizing feet comprising periodically contacting them with the solution of claim 14.

* * * * *